US006682732B1

(12) United States Patent
Blake et al.

(10) Patent No.: US 6,682,732 B1
(45) Date of Patent: Jan. 27, 2004

(54) TREATMENT OF LESIONS

(75) Inventors: David Russell Blake, Bath (GB); Clifford Robert Stevens, Wiltshire (GB); Robert Eisenthal, Bath (GB); Roger Harrison, Wiltshire (GB); Timothy Mark Millar, Bath (GB); Tulin Bodamyali, Wiltshire (GB); Janos Kanczler, Bath (GB)

(73) Assignee: The University of Bath, Bath (GB)

( * ) Notice: Subject to any disclaimer, the term of this patent is extended or adjusted under 35 U.S.C. 154(b) by 0 days.

(21) Appl. No.: 09/763,695

(22) PCT Filed: Aug. 27, 1999

(86) PCT No.: PCT/GB99/02844

§ 371 (c)(1),
(2), (4) Date: May 3, 2001

(87) PCT Pub. No.: WO00/12112

PCT Pub. Date: Mar. 9, 2000

(30) Foreign Application Priority Data

Aug. 28, 1998  (GB) ............................................... 9818913
Dec. 10, 1998  (GB) ............................................... 9827245

(51) Int. Cl.⁷ .......................... A61K 38/44; C12N 9/06
(52) U.S. Cl. ...................................... 424/94.4; 435/191
(58) Field of Search .......................... 435/191; 424/94.4

(56) References Cited

U.S. PATENT DOCUMENTS

| | | | |
|---|---|---|---|
| 4,105,800 A | * | 8/1978 | Jahns et al. .................... 426/61 |
| 4,320,116 A | | 3/1982 | Bjorck |
| 4,341,868 A | * | 7/1982 | Nakanishi et al. .......... 435/191 |
| 4,961,939 A | | 10/1990 | Antrim et al. |
| 5,310,541 A | | 5/1994 | Montgomery |
| 5,484,605 A | | 1/1996 | Scheiffele et al. |

FOREIGN PATENT DOCUMENTS

| | | |
|---|---|---|
| CA | 1167381 | 5/1984 |
| EP | 0518445 | 12/1992 |
| SE | 1546747 | 5/1979 |
| WO | 93/23080 | 11/1993 |
| WO | 95/22335 | 8/1995 |

OTHER PUBLICATIONS

McElroy, et al., A Symposium on Inorganic Nitrogen Metabolism Function of Metallo–Flavoproteins, The John Hopkins Press, Baltimore, pp. 500–507, 1956.
Bortolussi, et al., Relationship of Bacterial Growth Phase to Killing of Listeria Monocytogenes by Oxidateive Agents Generated by Neutrophils and Enzyme Systems, American Society for Microbiology, Infection and Immunity, vol. 55, No. 12, pp. 3197–3203, 1987.
Collins, et al., Histochemical Localization and Possible Antibacterial Role of Xanthine Oxidase in the Bovine Mammary Gland, Journal of Dairy Research, vol. 55, pp. 25–32, 1988.
Brunelli, et al., The Comparative Toxicity of Nitric Oxide and Peroxynitrite to *Escherichia Coli,* Archives of Biochemistry and Biophysics, vol. 316, No. 1, pp. 327–334, 1995.
Cooray, et al., Bactericidal Activity of the Bovine Myeloperoxidase System Against Bacteria Associated with Mastitis, Veterinary Microbiology, vol. 46, pp. 427–434, 1995.
Blake, et al., Xanthine Oxidase: Four Roles for the Enzyme in Rheumatoid Pathology, Biochemical Society Transactions, vol. 25, pp. 812–816, 1997.
Millar, et al., Xanthine Oxidase can Generate Nitric Oxide from Nitrate in Ischaemia; Viochemical Society Transactions, vol. 25, p. 528S, 1997.
Zhang, et al., Human Xanthine Oxidase Converts Nitrite Ions into Nitric Oxide (NO), vol. 25, p. 524S, 1997.
International Search Report GB 99/02844 Aug. 27, 1999.
UK Patent Office Search Report GB 9818913.7 Nov. 2, 1998.
Millar, T.M. et al. "Xanthine oxidoreductase catalyses the reduction of nitrates and nitrate to nitric oxcide under hypoxic conditions" *FEBS Letters* 1998 vol. 427 pp 225–228.
Shabani, M. et al. "Enhancement of wound repair with a topically applied nitric oxcide–releasing polymer" *Wound Repair and Regeneration* vol. 4 No. 3 pp 353–362.
Babior, B.M. et al. "Biological defense mechanisms. Evidence for the participation of superoxcide in bacterial killing by xanthine oxidase" *Journal of Laboratory Clinical Medicine* Feb. 1975, pp 253–244.
Crow, J.P. et al. "Sensitivity of the Essential Zinc–Thiolate Moiety of Yeast Alcohol Dehydrogenase to Hypchlorite and Peroxynitrite" *Biochemistry* vol. 34, No. 11, 1995 pp 3544–3552.
Moldoveanu, Z. et al. "Human Milk Peroxidase is Derived From Milk Leukocytes" *Biochemica et Biophsica Acta* vol. 718, 1992, pp 103–108.
Page, S. et al. "Xanthine oxidoreductase in human mammary epithelial cells: activation in response to inflammatory cytokines" Biochemica et Biophysica Acta, vol. 1381, 1998, pp 191–202.
Bjorck, L. et al. "Xanthine Oxidase as a Source of Hydrogen Peroxide for the Lactoperoxidase System in Milk" *Journal of Dairy Science,* vol. 62, 1979, pp 1211–1215.
Briley, M.S. et al. "Association of Xanthine Oxidase with the Bovine Milk–Fat–Globule Membrane. Nature of the Enzyme–Membrane Association" *Biochemistry Journal,* vol. 147, 1975, pp 417423.
Briley, M.S. et al. "Association of Xanthine Oxidase with the Bovine Milk–Fat–Globule Membrane. Catalytic Properties of the Free and Membrane–bound Enzyme" *Biochemistry Journal,* vol. 143, 1974, pp 149–157.

* cited by examiner

Primary Examiner—Jon P. Weber
(74) *Attorney, Agent, or Firm*—Merchant & Gould P.C.

(57) ABSTRACT

A composition for use in the treatment of lesions of the human or animal body comprises xanthine oxidoreductase and a pharmaceutically acceptable electron donor system. The composition can accelerate wound healing, especially in a hypoxic environment.

16 Claims, 3 Drawing Sheets

TREATMENT OF LESIONS

The invention relates to methods for the treatment, alleviation or prevention of lesions, especially ulcers, and in particular to means for use in any said method.

The term "lesion" is used herein to mean any interruption in the surface of the skin or in the surface of a membrane lining any cavity within the body, whether resulting from injury or disease. The term "ulcer" is used herein to refer to any breach on the surface of the skin or on the surface of a membrane lining any cavity within the body, which does not tend to heal quickly.

Human skin is a complex integration of different types of cells and tissues which form an organ. Skin is also the primary seat of the sense of touch and creates a covering for the protection of the deeper tissues. The skin also plays an important role in the regulation of body temperature and is also an excretory and absorbing organ. Skin consists primarily of a layer of vascular tissue and an external covering of epithelium known as the epidermis. Near the surface are the sensitive papillae, and alongside or imbedded beneath it are certain specialised organs, specifically the sweat glands, hair follicles, and sebaceous glands.

In order to protect the tissues below from trauma, the skin must be tough, flexible, and highly elastic. In the context of this function, injuries to the skin can occur. Wounds, which are caused by physical means, result in a disruption of the normal continuity of the structures of the skin. Examples of wounds include cuts, punctures, lacerations, etc. There are two types of healing processes:

(1) primary union or first intention healing and
(2) secondary union or second intention healing.

Primary union occurs when a clean wound with a minimal loss of tissue heals together cleanly. The process involves clotting and formation of a crust or scab to seal the wound; an acute inflammatory reaction, reepithelialization of the surface and fibrous bridging due to fibrin followed by complete sealing of the wound by an epithelial covering. Thereafter, hair follicles, sebaceous glands and sweat glands may subsequently regenerate. The process of second intention healing requires the removal of necrotic debris. The gap in the wound then fills in with fibrous materials. Second intention healing can be impaired by infection and by a restriction, for whatever reason, of the blood supply and therefore oxygenation status of the wound to give rise to ulcers. This invention is concerned, inter alia, with the treatment of those ulcers, which are exemplified by decubitus ulcers, described below.

In nursing homes, hospitals or in private homes where invalid patients with certain diseases and afflictions are bedridden, a problem arises from bed sores which these patients develop. These bed sores, which have a tendency to ulcerate and may also be known as decubitus ulcers, usually result from a loss of blood circulation caused by pressure on the skin, particularly pressure over a bony protuberance. Decubitus means ischaemic necrosis of the skin or subcutaneous tissue caused at a projected bone area due to continuous pressure. It is commonly developed in aged patients as a result of such patients being confined to their beds over long periods of time, and may also be developed on compression in plaster upon fracture.

Decubitus ulcers are defined by reference to four "Stages" according to severity: Stage I—Skin pink-mottled, the epidermis is damaged; Stage II—Skin is cracked, blistered and broken, the epidermis is destroyed; Stage III—Skin is broken with some tissue involvement, the sub-cutaneous skin is destroyed and there are decaying cells; Stage IV—Extensive penetration to muscle and bone, presence of necrotic tissue, and profuse drainage, structures are decayed. By stage III or IV, debridement is usually necessary.

The pressure on areas of support may exceed the mean capillary blood pressure, with the result that those areas are vulnerable to the formation of decubitus ulcers. Other factors which can contribute to formation of decubitus ulcers are lack of proper ventilation, moisture and diet. Additionally, the problem of bed wetting and the accumulation of urine in the bed contribute to the formation of bed sores since the moisture remains in the area of the patient's body. Attempts have been made to remedy these conditions and thereby prevent the decubitus ulcers. Some have involved merely the passing of air through the bed mattress which air is then allowed to pass upwardly around the patient's body. Other devices have had pulsatingly inflatable air mattresses which again merely allow the air to be circulated upwardly around the body of the patient. Those attempts have been relatively unsuccessful in practice.

Some supportive measures used for the prevention or alleviation of decubitus are: occupational therapy, physical therapy, and nutritional therapy. For example, it is the practice to change the position of a patient or to release one or more pressed areas of the patient from pressure so that his skin is protected from continuous compression. Typically, that involves a repositioning schedule every two hours, checking bony prominences for breakdown daily, keeping skin dry and clean, ambulating the patient as much as possible, forcing fluids, and using cornstarch to prevent friction. Other known practices are use of a special bed having a hygroscopic cushioning material and effecting rigorous skin cleaving and wiping, with the object of keeping the skin dry and thereby preventing secondary infection. Where the condition of decubitus is extremely serious, surgery is effected to resect the decubital part and then to restore the resulting lost part by sutured minification, adjacent flap, distant flap or the like.

There are many different products available for the care of decubitus ulcers, including solutions having antibacterial or antacid activity, water-repellent ointments, and dressings. For example, Betadine solution rinses are used for their antibacterial properties, but some allergic reactions can occur to the iodine, enhancing the skin problem. Uniwash and Uniderm treatments have to be done every eight hours or more frequently. Dressings are necessary and beneficial but sometimes tear the skin further. Medicated dressings such as Silvadene have to be changed also every eight hours. Domeboros Solution is used every four hours during the day. Antacids may be beneficial for superficial ulcers, but can hold in purlent matter and debris in the deep ulcer.

Patients particularly prone to formation of decubitis ulcers are cachetic patients (those in negative nitrogen balance), patients with congenital or acquired boney deformities, stroke patients who are immobile, paraplegics with uncontrollable muscle spasms, any spinal cord injury patient, incontinent patients, arthritic patients, those who are confused or comatose, nutritionally deficient patients, those with oedema or poor capillary refill, anyone who is on medications such as steroids, tranquilizers and analgesics, any geriatric patient, and anyone with pre-existing diseases. Decubiti in such patients may also result from or be exacerbated by friction, shearing force and pressure, which all hospital patients are exposed to while in bed. Usually, a combination of two of those forces will cause a pressure sore, which may appear within twelve hours. Friction can be from moving in bed, shearing can be from a position in bed, and pressure can be from gravity alone. A pressure of greater than 25 mm Hg. will occlude flow of blood to capillaries in soft tissues causing hypoxia and, if unrelieved, eventual necrosis which is manifested in decubitis ulcer formation.

Decubitus remains a skin disease which is difficult to prevent in patients who are immobile for a substantial length of time, even with intensive nursing attendance. Whilst the causes, observable symptoms and modes of treatment of ulcers in other membranes may differ substantially from those of decubitis, a common factor is the tendency of ulcers not to heal, or to heal only very slowly. Moreover, once ulceration has occurred, it remains difficult to cure, and can result in long and severe pain to patients. There remains a need for improved means of treating, alleviating and preventing the formation of ulcers, especially decubitis ulcers, as well as other types of lesion, for example, neoplastically transformed lesions, other lesions that may be virally infected, and warts.

The invention provides a composition for use in the treatment of lesions of the human or animal body, the composition comprising XOR and a pharmaceutically acceptable electron donor system. Xanthine oxidoreductase exists in two inter-convertible forms, xanthine dehydrogenase (XDH, EC 1.1.1.204) and xanthine oxidase (XO, EC 1.1.3.22). XDH, which is believed to predominate in vivo, preferentially reduces $AND^+$, whereas XO does not reduce $AND^+$, preferring molecular oxygen. Where reference is made herein to "XOR", that term includes xanthine oxidoreductase, which is to be understood as referring to both xanthine dehydrogenase (XDH) and xanthine oxidase (XO), where appropriate. It will be appreciated that references to XOR further include references to analogs of xanthine oxidoreductase that have xanthine oxidoreductase activity. Such analogs may include but are not limited to, for example, xanthine oxidoreductase which has been modified chemically or otherwise, analogs having fragments of xanthine oxidoreductase derived from naturally-occurring enzyme, and analogs having polypeptides obtained by replication of the enzyme or a portion thereof using any suitable biotechnological method, provided in each case that the catalytic activity of the endogenous xanthine oxidoreductase is retained at least to an appreciable extent.

References herein to xanthine oxidoreductase are furthermore to be understood as embracing material of any biological origin, for example, of mammalian or other animal origin, or originating from a suitable micoorganism, for example, aspergillus sp. Xanthine oxidoreductase of ruminant origin offers the advantage of ready availability.

The inventors have found that, unexpectedly, compositions according to the invention containing XOR and a pharmaceutically acceptable electron donor system have antiseptic properties and recuperative activity which will render them suitable agents for use in the treatment of lesions, including ulcers, for example, decubitus ulcers, ischaemic leg ulcers, diabetic foot ulcers, genito-urinary ulcers, ulcerative keratitis and ulcers of mucosal surfaces of the mouth and the like, neoplastically transformed lesions, virally infected lesions, warts, and lesions of the mucous membrane. Whilst the mode of action of the compositions is not known with certainty, it is believed that they may assist in the formation of granulation tissue in such conditions. Moreover, at least in the case of patients affected with decubitus ulcers, ischaemic leg ulcers, diabetic foot ulcers, genito-urinary ulcers and ulcerative keratitis and the like, it is believed that the compositions assist in increasing the local perfusion.

The enzyme xanthine oxidoreductase is a complex molybdoflavoprotein, the action of which has been studied for many years. It is a major protein component of the membrane surrounding fat droplets in whole milk. Consequently, cows' milk is a rich and convenient source of the enzyme. Xanthine oxidoreductase has also been characterised from rat, chicken and turkey livers. Human milk has also been found to contain xanthine oxidoreductase.

In the treatment of ulcerative lesions, especially decubitus, it may be preferred for the composition to be used in combination with means for enclosing in airtight manner the lesion with the applied composition.

The composition of the invention may comprise one or more pharmaceutically acceptable excipients or carriers. The composition of the invention may be suitable for topical administration. Advantageously, the composition is suitable for topical application to the skin. The composition may advantageously be suitable for topical application to the cornea.

The composition may be used in a prophylactic method for the prevention of ulcers, or in a method of treatment of ulcers, especially decubitis ulcers. As already mentioned, the compositions of the invention may be used in the treatment of ulcerative keratitis. It has been found that small amounts of xanthine oxidoreductase may naturally be present on the cornea, the enzyme apparently being secreted from the lachrymal glands. The amount of enzyme secreted in a diseased eye is reduced, but may in accordance with the invention be augmented by application of a composition comprising XOR and an electron donor system.

The inventors have also found that small amounts of xanthine oxidoreductase are produced in the salivary glands and secreted in the mouth, and it is thought that the enzyme may play a part in defending the mucosal surfaces of the mouth from infection. The composition of the invention may be effective in the treatment of ulcers of the mucosal surfaces of the mouth.

The composition may be used in the treatment of neoplastically transformed lesions. The composition may be used in a prophylactic method for the prevention of, or in a method of treatment of, cervical cancer. As is well-known, cervical cancer is generally preceded by the occurrence of neoplastically transformed lesions which, if left untreated, in a large proportion of cases lead to development of cervical cancer. The inventors have found that xanthine oxidoreductase is naturally present in the healthy cervix. It is thought that the enzyme, generation of which varies with polymorphisms in the gene, may play a role in the prevention of infection in the cervix. The generation of the enzyme may be inhibited where a viral infection does occur. The diminished production of enzyme in situ may thus, in accordance with the invention, be augmented by application of a composition comprising XOR.

The invention further provides a dressing for application to a part of a human or animal body, comprising a substrate and a pharmaceutical composition retained on a surface of or within the substrate, the pharmaceutical composition comprising XOR and an electron donor system. Advantageously, the dressing comprises a layer of material which is impermeable to air, that is, which, when in use the dressing is applied to the part of the human or animal body, substantially prevents the passage of ambient air through the dressing to the said part.

There have been suggestions that xanthine oxidoreductase has a role in the production of bactericidal agents. In the presence of oxygen, xanthine oxidoreductase can catalyse the production of superoxide and hydrogen peroxide, which are known bactericidal agents. Bactericidal levels of superoxide or hydrogen peroxide are, however, unlikely to be attained at low oxygen concentrations.

It has been reported, Millar, T. M. et al, FEBS Letters 427 (1998) 225–228, that, under hypoxic conditions and in the presence of NADH, XOR is capable of catalysing the reduction of glyceryl trinitrate (GTN), as well as inorganic nitrate and nitrite, to nitric oxide (NO).

Nitric oxide (NO) is widely recognised as mediating the relaxation of smooth muscle in vasodilation and as initiating many other important biological functions, including inhibition of platelet aggregation and adhesion. Its generally accepted physiological source is NO synthase, a complex enzyme which is totally dependent on oxygen as one of its substrates for its activity and consequently ineffective in a hypoxic environment, where the vasodilatory properties of NO might be seen to be advantageous.

Hypoxic conditions may be present in some types of lesions, in particular, where the supply of oxygenated blood may be disrupted or prevented and/or where the lesions are enclosed in airtight manner, for example, using a dressing that is impermeable to air. In neoplastically transformed lesions of the cervix the conditions may also be hypoxic, the cervix having an intrinsically relatively low oxygen concentration.

We have found that the optimum pH for the production of NO from XOR under hypoxic conditions is about pH 5.5. Thus, we have found that lesions, especially ulcers, present an environment in which the production of NO in the presence of XOR would be at or near a peak.

At pH levels above about 4 pathogenic bacteria are more active than at lower pH values. It is postulated that, under conditions prevailing in lesions, especially ulcers, XOR can catalyse the production not only of superoxide, but of NO. Superoxide and NO rapidly interact to generate peroxynitrite, a much more potent bactericidal species than superoxide, NO or hydrogen peroxide. While superoxide has some bactericidal properties and in some situations NO has also been found to kill or damage bacteria, it is the interaction of superoxide and NO to form peroxynitrite and other products which is believed to give superior bactericidal action. Peroxynitrite (and, it is thought, other products of the interaction of superoxide and NO) are particularly potent bactericidal species.

The concentration of nitrite present in lesions is normally low, and it might therefore be thought that the potential for XOR-catalysed generation of NO would be limited. It is believed however that, the known affinity of XOR for acidic polysaccharides such as those occurring in bacterial capsules causes XOR to become more concentrated in the immediate vicinity of bacteria. In anaerobic environments, bacteria commonly are found to excrete nitrite and thus the association of XOR with the bacteria may have the result that the XOR will be located in a localised region of elevated nitrite concentration.

Whilst it is thought that it is the peroxynitrite formation that gives rise to the desirable bactericidal action of XOR in hypoxic conditions, it may in certain applications, for example, ulcerative keratitis be superoxide that is the predominant bactericidal species. In some circumstances, it will be desirable to maintain or promote a hypoxic environment in the region of application of the XOR-containing composition, thereby favouring the peroxynitrite pathway, whilst in others, such as in the treatment of ulcerative keratitis that may be unnecessary or even undesirable.

From the above it will be appreciated that the active XOR may be regarded as a "natural antibiotic", that is, a substance of natural origin which is capable of destroying or inhibiting the growth of at least some strains of pathogenic micro-organism.

The substrate may itself constitute the impermeable layer. Preferably, the dressing comprises a substrate layer and an impermeable layer to which the substrate layer is attached. It will be appreciated, however, that the dressing of the invention will not necessarily include means for airtight sealing, it being possible for such sealing means to be provided separately, for example, in the form of an impermeable plastics film or a conventional airtight dressing. Advantageously, the substrate is an absorbent material. The substrate may be of any suitable material that is dermatologically acceptable. It will be appreciated that it will be desirable for the dressings to be sterile when applied to the body. Accordingly, the substrate should be one that will withstand any sterilisation method to which the dressing will be subjected, and the substrate material will thus be selected having regard to the sterilisation method to be used. Advantageously, the substrate comprises collagen or freeze-dried calcium alginate. The substrate may be collagen fibril matting.

Advantageously, the xanthine oxidase is present in an amount of about 0.1 $\mu$g to 1 mg, preferably 10 $\mu$g to 1 mg, per g of the substrate.

In the compositions or dressings according to the invention, the xanthine oxidase is advantageously in lyophilised form. It will be appreciated that the method of isolation of the XOR for use in accordance with the invention will need to be so selected that the activity of the XOR is wholly or at least substantially retained. In general, such methods should not include any step in which the temperature of the XOR exceeds 65° C. Advantageously, the electron donor system comprises at least one nitrogen-containing compound, which may be a heterocyclic compound. The nitrogen-containing compound may advantageously be selected from the group consisting of purines, nicotinamides, and derivatives thereof. Examples of suitable electron donors are NADH and hypoxanthine. There may also be an electron acceptor system present, for example, the composition may include one or more compounds selected from organic or inorganic nitrates and nitrites, for example, glyceryl trinitrate or isosorbyl dinitrate.

The invention also provides a method for the treatment of lesions, for example, decubitus, ischaemic leg ulcers, diabetic foot ulcers, genito-urinary ulcers and ulcerative keratitis and the like in a patient, which comprises administering to said patient a pharmaceutical composition comprising an effective amount of xanthine oxidase and a pharmaceutically acceptable electron donor system, wherein the method of administration comprises bringing the pharmaceutical composition into contact with the ulcers of said patient and effecting substantially airtight sealing of the ulcer and the composition in contact therewith from the ambient atmosphere. Advantageously, the composition is impregnated into a suitable packing substrate. The substrate may be selected from freeze-dried calcium alginate or collagen fibril matting.

The dosage administered will be dependent upon the age, health and weight of the recipient, kind of concurrent treatment, if any, frequency of treatment and the nature of the effect desired. For example, dosage forms for topical administration include about 0.1 $\mu$g to 1 mg, and advantageously 10 $\mu$g to 1 mg, of xanthine oxidase per gram of carrier. The dosages in the treatment of lesions other than ulcers may be similar to those required for ulcers. The composition may be in the form of a cream, gel, solution (including an injectable solution), ointment or any other suitable form, according to the nature and location of the lesion to be treated. The composition may advantageously be in the form of a gel that liquefies at body temperature. Such a gel may, for example, be pplied to an alginate substrate before application to the lesion to be treated, or may be incorporated into a dressing. The XOR may be present in those dosage forms in an amount of 0.1 µg/ml to 1 mg/ml and preferably 10 µg/ml to 1 mg/ml. The composition may contain other active ingredients, if desired. In the case of treatment of the cornea, it may be appropriate for the composition to be included in, for example, a lubricant solution administrable as eye drops.

Before the impregnated material is applied to a patient, it is preferable to wash the sore with a suitable washing compound. In practice, the composition and dressing of this invention will normally be used only after removal of any necrotic tissue that is present. Proper removal of necrotic tissue will normally be done under the supervision of a physician and may include surgical debridement.

The invention further provides a system for use in the treatment of lesions, having at least two components, a first component of the system comprising XOR and a second component of the system comprising an electron donor system, said first and second components being arranged for application to a surface of an animal or human body in combination or separately, simultaneously or sequentially.

The compositions and dressings of this invention have many advantages because of their combination of ingredients and the minimal accompanying treatment of the patient that is required. It is believed that the properties of the packing that are beneficial are as follows: antiseptic action through the generation of superoxide, nitric oxide and peroxynitrite by the enzyme xanthine oxidase, tonal, topical stimulation giving rise to increased circulation at the base of ulcers leading to increasing granulation tissue and thus accelerated healing.

The invention will now be explained in more detail, with reference to the accompanying drawings, in which FIG. 1 is a graph illustrating the effect of peroxynitrite cell viability under the conditions of Test 6(*a*); and FIG. 2 is a graph illustrating the dependence of XO-mediated killing of cells as determined in Test 6(*b*).

DETERMINATION OF NITRIC OXIDE PRODUCTION

Figure 1:
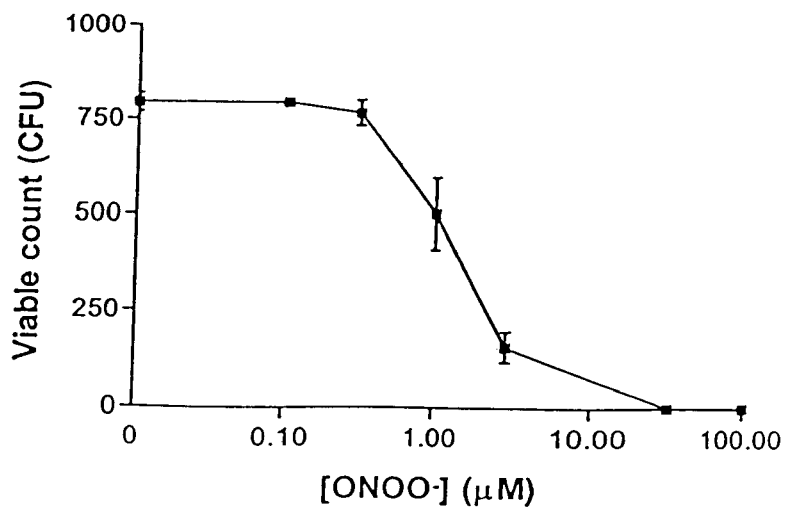

The production of nitric oxide in the following tests and examples was analysed using an ozone chemiluminescence assay in a continuous flow apparatus (Sievers NOA 280) that allows the real time analysis of NO production. The apparatus was modified to allow a constant stream of nitrogen to flow into the reaction chamber. Chemiluminescence data were collected by a data acquisition system; the mean NO produced in parts per billion (ppb) was calculated from readings taken every second and shown as NO ppb/s. Progress curves, of molar production of NO against time, were calculated by taking into account the gas flow and successively integrating the ppb/s curves. Reactions were carried out in a final volume of 1 ml at 37° C. in an atmosphere of <1% oxygen (Stathkelvin combination needle oxygen electrode, Diamond General Corp.).

The method used was as follows:

(a) Two clean 7 ml bijous were obtained, one for each of the "substrates" and the "milk".

To the "substrates" bijou, 200 µof 100 mM stock sodium nitrite was added together with 200 µl of the 5 mM reduced NADH to give an assay concentration of 20 mM nitrite and 1 mM reduced NADH. To the "milk" bijou were added 600 µl of milk sample to give an assay volume of 1 ml.

(b) Using a flow rate of 200 ml/min, the bijou mixture and a corresponding injection needle was degassed with nitrogen gas ($N_2$) for about 10 seconds and the bijou was capped.

(c) The reaction cell comprised a 7 ml screw-cap bijou having three needle holes in its cap. A continuous flow of warmed $N_2$ (200 ml/min flow rate) was injected into the bijou through one of the needle holes in the cap to give the required hypoxic conditions. The reaction cell was held at a temperature of 37° C. in a water bath mounted on a magnetic stirrer. A magnetic flea was placed in the reaction cell to mix the samples once injected.

(d) Samples of NO were taken from the reaction cell by a needle that was connected to a Sievers Nitric Oxide Analyser (NOA-280) and the results were recorded for analysis using a computer.

(e) At time (t) 0 minutes, the NOA-280 started the measurement of NO from the reaction cell. At t=1 minute, the contents of the "substrates" bijou were injected into the reaction cell using a 1 ml syringe and the background NO was measured.

(f) At t=5 minutes, the contents of the "milk" bijou were injected into the reaction cell using a 1 ml syringe and the release of NO was monitored for a further 20 minutes. The set up was such that the reaction cell was a sealed system having an inlet gas flow of 200 ml/min and a sample extraction flow to the NOA-280 of 200 ml/min. The steady-state generation of NO (which corresponded to a plateau region on the trace of the NO production) was noted to give the mV/s release of NO from the 1 ml assay volume.

The samples were diluted with PBS where necessary to give an assay of 1 ml for the test of NO generation. In Tests 1 to 5, the enzyme-coating mixture and substrates mixture were combined before introduction into the reaction cell, but the measurement method was otherwise as described above.

Reagents Used

The reagents used in the tests and examples described below were as follows:

1. Bovine xanthine oxidase (XOR) Biozyme, Blaenavon, UK. This source of enzyme had a concentration of 10.7 mg/ml and was batch 104AX 2. Sodium nitrite ($NaNO_2$)—Sigma Chemicals (Sigma-Aldrich Company Ltd.), Poole, UK. This was dissolved in 1X Phosphate Buffered Saline (PBS), pH 7.3, to the required concentration.

3. β-Nicotinamide Adenine Dinucleotide, reduced form, (P-NADH)—Sigma Chemicals.

4. Phosphate Buffered Saline (PBS)—Oxoid Ltd., Basingstoke, UK. Tablets were added in the proportion of 1 per 100 ml of distilled water and mixed until thoroughly dissolved to give 1X PBS, pH7.3.

5. Oxypurinol—Sigma Chemicals. A stock 1 mM solution was made up by adding 0.00159 to 0.25 ml of 1M NaOH. This was mixed until the oxypurinol dissolved. Then 9.75 ml of 1X PBS was added and the pH altered until pH7.3 was reached using drops of 1M Hl.

6. Diphenyliodonium (DPI)—ICN Biomedical. A stock 1 mM solution was made up by adding 0.0032 g to 10 ml 1X PBS, pH7.3.
7. Human Breast Milk (source of active XOR). Samples obtained from subjects in the local area Test 1

The release of nitric oxide (NO) from a composition including pure bovine xanthine oxidase under hypoxic conditions was studied. The samples studied comprised reduced β-Nicotinamide adenine dinucleotide (NADH) and nitrite ($NO_2^-$) and pure bovine xanthine oxidase.

Bovine xanthine oxidase was diluted with PBS as indicated in Table 1 below to give 300 µl of enzyme mixture. The enzyme mixture (300 µl) was mixed with 700 µl of a substrate mixture to give an assay volume of 1 ml. The substrate mixture comprised nitrite which was added to the assay to give a concentration of 1 mM and NADH which was added to give a concentration of 0.3 mM. Where, for example in Tests 2 to 4 below, additional components are added to the sample, the amount of PBS is adjusted accordingly to give an assay volume of 1 ml. The total XOR protein in the assay is shown in Table 1. The sample was placed in the reaction vessel of the NO determination apparatus under a nitrogen atmosphere and the generation of NO was measured and the results calculated as a steady state rate in mV/s. The rate of NO release for the different concentrations of XOR is also shown in Table 1.

TABLE 1

| Volume XOR enzyme (µl) | Volume PBS (µl) | XOR protein in assay (µg) | NO release (mV/s) |
|---|---|---|---|
| 0 | 300 | 0.0 | 15.10 |
| 2 | 298 | 21.4 | 50.05 |
| 5 | 295 | 53.5 | 76.35 |
| 10 | 290 | 107.0 | 128.55 |
| 15 | 285 | 160.5 | 187.20 |
| 20 | 280 | 214.0 | 225.75 |

Where the pure XOR is used in the samples, NADH was required as a substrate for the reduction of the nitrite to proceed.

Test 2

Using the method described above in respect of Test 1, the effect of the variation in the concentration of NADH on the production of NO was investigated. 4 mM NADH was diluted with PBS to give the relevant concentration. The results are shown in Table 2.

TABLE 2

| XOR protein in assay (µg) | NADH concentration in assay (mM) | NO release (mV/s) |
|---|---|---|
| 53.5 | 0.00 | 0.00 |
| 53.5 | 0.10 | 30.45 |
| 53.5 | 0.25 | 66.80 |
| 53.5 | 0.50 | 92.55 |
| 53.5 | 1.00 | 103.35 |
| 53.5 | 2.00 | 109.20 |
| 107.0 | 0.00 | 0.00 |
| 107.0 | 0.10 | 74.45 |
| 107.0 | 0.25 | 142.70 |
| 107.0 | 0.50 | 192.65 |
| 107.0 | 1.00 | 230.05 |
| 107.0 | 2.00 | 264.65 |

Test 3

Using the method described above in respect of Test 1, the effect of the variation in the concentration of nitrite on the production of NO was investigated. As for Test 1, the concentration of NADH was 0.3 mM. 1M nitrite (or 100 mM nitrite, where appropriate for low concentrations) was diluted with PBS to give the relevant concentration. The results are shown in Table 3.

TABLE 3

| XOR protein in assay (µg) | Nitrite concentration in assay (mM) | NO release (mV/s) |
|---|---|---|
| 21.4 | 0 | 0.00 |
| 21.4 | 1 | 53.75 |
| 21.4 | 5 | 184.8 |
| 21.4 | 10 | 378.10 |
| 21.4 | 25 | 407.55 |
| 21.4 | 50 | 474.05 |

Test 4

The method of Test 1 was repeated with known inhibitors of XOR included in the assay to show that the NO generation was being catalysed by XOR. Two different inhibitors were used. Oxypurinol was used at a concentration of 100 µM. Oxypurinol is a molybdenum site-specific inhibitor. Diphenyliodonium (DPI) was used at a concentration of 100 µM. DPI is a FAD site inhibitor. The results are shown in Table 4.

TABLE 4

| Inhibitor | NO release (mV/s) |
|---|---|
| 100 µM Oxypurinol | 0.00 |
| 100 µM DPI | 0.00 |

There was no release of NO in the presence of the XOR inhibitors.

Test 5

Human breast milk was assayed with 2 0mM nitrite and 1 mM NADH using the method as described above. The human breast milk was collected on several days post partum and frozen at −20° C. 600 µl of milk was used in each test.

The generation of NO was investigated using the method described above. The results are given below in Table 5. This test demonstrates NO release under hypoxic conditions using a known source of active xanthine oxidoreductase.

TABLE 5

| Days post partum | protein content (µg/ml) | NO release (mV/s) |
|---|---|---|
| 7 | 411.26 | 40.45 |
| 30 | 683.05 | 60.75 |
| 36 | 561.49 | 42.48 |
| 66 | 305.52 | 27.80 |
| 158 | 110.84 | 29.80 |

Test 6

To obtain cells used in this test, the infective bacterial strain Escherichia coli NCTC 86 (*E.coli*) was cultured on nutrient agar at 37° until colony formation occurred, usually overnight. This stock culture was used for subsequent experiments including sub-culturing in nutrient broth and plated onto agar weekly. Experimental cultures of *E.coli* were set up overnight in nutrient broth from single colonies on an agar plate. Cells were harvested and counted using a standard curve of known absorbance at 470 nm against viable cell count. Peroxynitrite was generated by the method of Crow et al BIOCHEM. 34 pages 3544 to 3552 (1995). In accordance with that method, a mixture of sodium nitrite and hydrogen peroxide was reacted under acid conditions then immediately quenched by the addition of sodium hydroxide. The concentration of $ONOO^-$ formed was measured using an absorption coefficient of 1670 $M^{-1}$ $cm^{-1}$ in a spectrophotometer at a wavelength of 303 nm. Solutions of different concentrations for use in (a) below were obtained by dilution of the product solution using PBS.

6(a) Peroxynitrite Effect on Cell Viability

Cells cultured as described above were diluted to suitable working concentrations ($10^4$–$10^5$ Cells $Ml^{-1}$) in sterile phosphate buffered saline (PBS). $ONOO^-$ at a range of concentrations from 100 $\mu M$ to 0.01 $\mu M$ was added as a bolus dose to cells and incubated at room temperature for ten minutes. Aliquots were taken from the cell cultures and plated on to nutrient agar and incubated in a warm room at 37° C. overnight. Viable cells formed colonies on the agar and were counted. The number of colonies formed was related to an untreated control and a graph of the results is shown in FIG. 1, which illustrates the effect of $ONOO^-$ on cell viability. The decrease in viable count with increasing concentration of $ONOO^-$ in FIG. 1 is indicative of a profound inhibitory effect.

Peroxynitrite has also been shown to reduce viability in *S. enteritidis* under similar conditions to those indicated above. $IC_{50}$ values of peroxynitrite in respect of *E. coli* and *S. enteritidis* (that is, the concentration that reduces viability to 50% of control viable count of the respective cell type) of 1.402 and 2.026 $\mu M$ were determined under the conditions used. Peroxynitrite-mediated killing has also been indicated in the case of Gram positive bacteria, in a test in which incubation of Straphylococcu aureus with SIN-1 (3-morpholinosydnonimine, which releases both superoxide and NO simultanteously on hydration) showed reduced growth in dependence on the amount of added SIN-1.

6(b) Effect of Xanthine Oxidase Derived Species on Cell Viability

Figure 2:
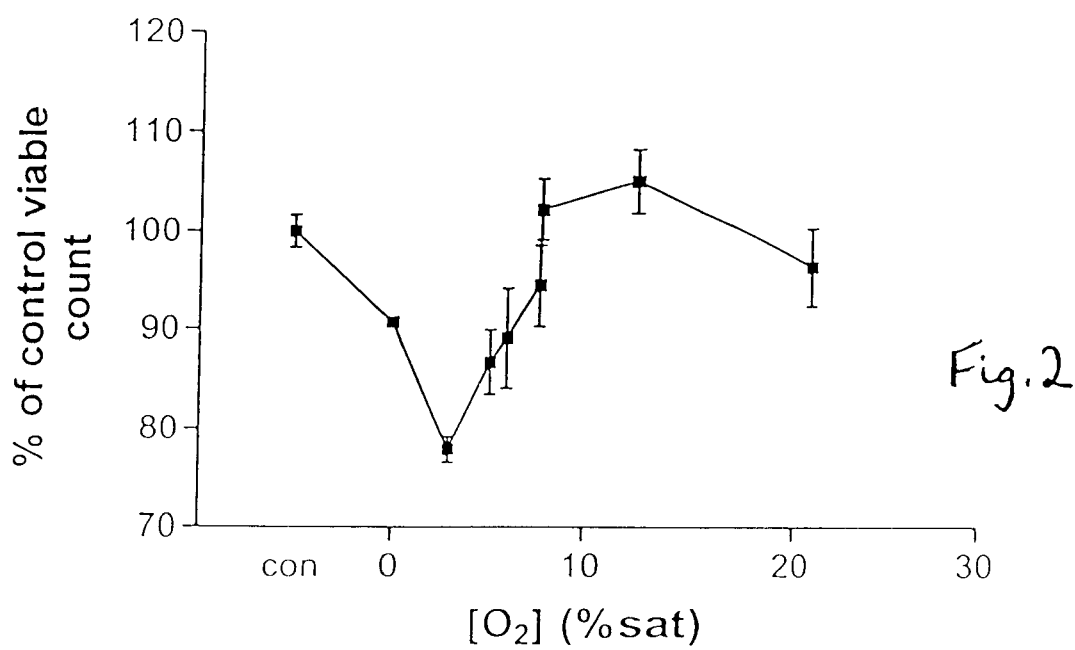

*E.coli* were cultured as described above. Aliquots were taken and incubated with a reaction system consisting of bovine Xanthine oxidase (XO) (53.2 $\mu gml^{-1}$), nicotinamide adenine dinucleotide in reduced form (NADH) (300 $\mu M$), sodium nitrite, ($NaNO_2$) 1 mM and oxygen at a range of concentrations. Desired oxygen concentrations were generated by delivery of a mixture of oxygen and nitrogen in appropriate proportions and determined using a Clark type $O_2$ electrode. This reaction was followed at 37° C. for 30 min with mixing before an aliquot was taken and plated onto agar and incubated in a warm room at 37° C. Viable cells formed colonies on the agar and were counted. Viable cell counts were performed in triplicate and the results expressed as a percentage viable count in each case related to a non enzyme control of the same oxygen concentration. The results are shown in FIG. 2, which suggest that XO-mediated killing of cells is occurring. The most effective killing (indicated by the lowest viable cell count) is at an oxygen concentration of approximately 3% of saturation. The range of oxygen tensions used covers those in which XO has previously been considered to be active, namely superoxide generation (21% $O_2$ saturation) and nitric oxide production (0% $O_2$ saturation). A certain amount of killing is seen at both of these extremes as compared with control samples. However, it is only at an intermediate oxygen concentration that the greatest amount of killing is observed. This suggests a role for peroxynitrite mediated killing which has been generated in this system by the enzyme xanthine oxidase.

Corresponding data obtained in respect of *S. enteritidis* indicated a peak killing oxygen concentration of 0% for that cell type. For both *E. coli* and *S. enteritidis* the viability increases with oxygen concentration with little or no killing above about 8% oxygen, although some limited killing (about 5% and about 10% for the respective cell types) is again observed at higher oxygen concentrations of about 21%.

Replacement of NADH in the above method by 100 $\mu M$ hypoxanthine, with a sodium nitrite concentration of 2.5 $\mu M$ led to slightly higher peak killing oxygen concentrations (6.4% for *E. coli* and 1.5% for *S. enteritidis*). More limited killing was also observed using xanthine instead of hypoxanthine. The XO/hypoxanthine combination was also found to reduce the growth rate of Lactobacillus in a dose dependent manner for both hypoxanthine and XO. Addition to the XO/hypoxanthine system of superoxide dismutase at oxygen concentrations in the range of from 0 to 2% was found to increase the amount of measurable NO (as a result of removal of superoxide by superoxide dismutase), providing a further indication of the hypothesis that peroxynitrite formation from NO and superoxide occurs in the XO/hypoxanthine system.

6(c) Effect of Peroxynitrite Scavenger on Bacterial Growth

*E. coli* were seeded into nutrient broth at $2.10^7$ cell $ml^{-1}$ and incubated at 37° C. under atmospheric air conditions (that is, 21% oxygen saturation). Four separate test samples of volume 1 ml were prepared by addition at 1 hour of incubation as follows:

1 Peroxynitrite at concentration 100 $\mu M$.
2 Peroxynitrite at 100 $\mu M$ and quercetin (peroxynitrite scavenger) at 100 $\mu \mu M$.
3 Xanthine oxidase (53.2 $\mu g$) and xanthine at 100 $\mu M$.
4 Xanthine oxidase (53.2 $\mu g$) and NADH at 100 $\mu M$.

Corresponding controls were also prepared, and the growth curves generated over time determined by monitoring absorbance. Sample (1) showed strong killing, but the presence of quercetin (sample (2)) had a clear effect in reducing killing, pointing towards peroxynitrite mediation of killing. XO/NADH (sample (4)) and XO/xanthine (sample (3)) showed limited, but significant, growth retardation effects.

The result of part (a) of this test appears to confirm the bactericidal potency of the peroxynitrite species. Part (b) above supports the hypothesis that, under appropriate conditions, XOR can catalyse production both of superoxide and of NO, interaction of those two products giving rise to peroxynitrite, and possibly other interaction products that may have similar bactericidal activity to peroxynitrite. The oxygen concentration of less than 8% at which maximum killing was observed is believed to be similar to that obtaining in ulcers.

6(d) Effect of XO and Hypoxanthine Incubation on Bacterial Growth Rate.

Bacteria were seeded into nutrient broth (NB) and grown over night at 37° C. The culture was then counted and normalised to give a final cell concentration of $1.8 \times 10^7$ cells $well^{-1}$ into the wells of a 96 well plate in fresh nutrient broth. The optical density of each well was monitored every 15 minutes as a measure of the growth rate of each bacterial species. Growth curves were generated for each species and the maximal rate of growth (logarithmic phase) was measured. Cells were treated to a range of experimental conditions in which the growth rate of cells was related to a control of untreated cells. The results were expressed as a percentage of the growth rate of the control cells.

Figure 3:
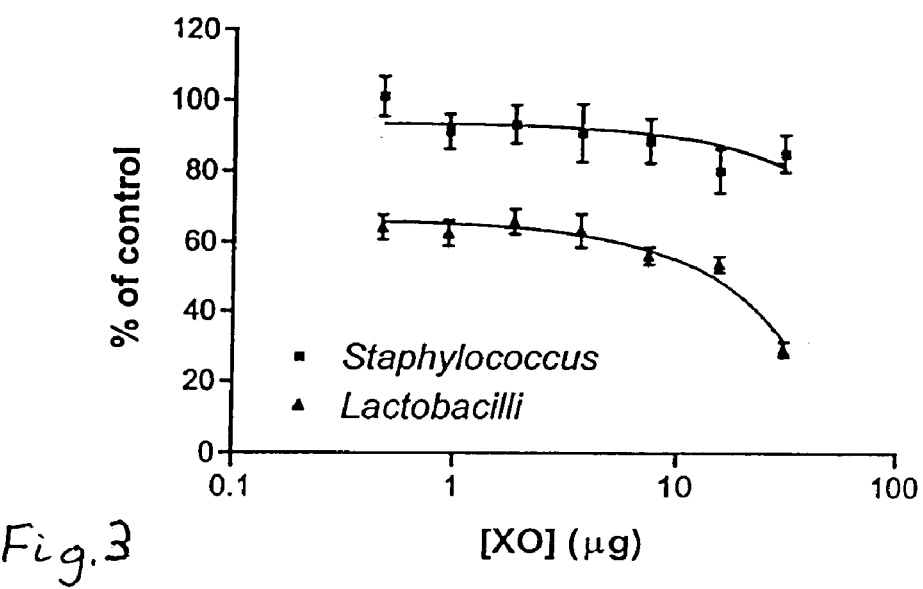
FIG. 3 is a graph showing the effect of XO concentration on bacterial growth.

(i) At a fixed concentration of hypoxanthine (100 $\mu$M) a range of purified XO protein concentrations were added at time 0 minutes. The optical density was followed and the growth rate calculated. The effect of enzyme concentration is shown in FIG. 3 for Staphylococcus aureus 6751 and Lactobacillus casei 6375. The growth rate of both Staphylococcus and Lactobacilli was reduced compared to the control. Lactobacillus growth rate was reduced with a half maximal concentration of XO (that is, the concentration at which the cell growth was 50% of control) being about 14 $\mu$g. A less marked growth inhibition was observed for Staphylococcus.

Figure 4:
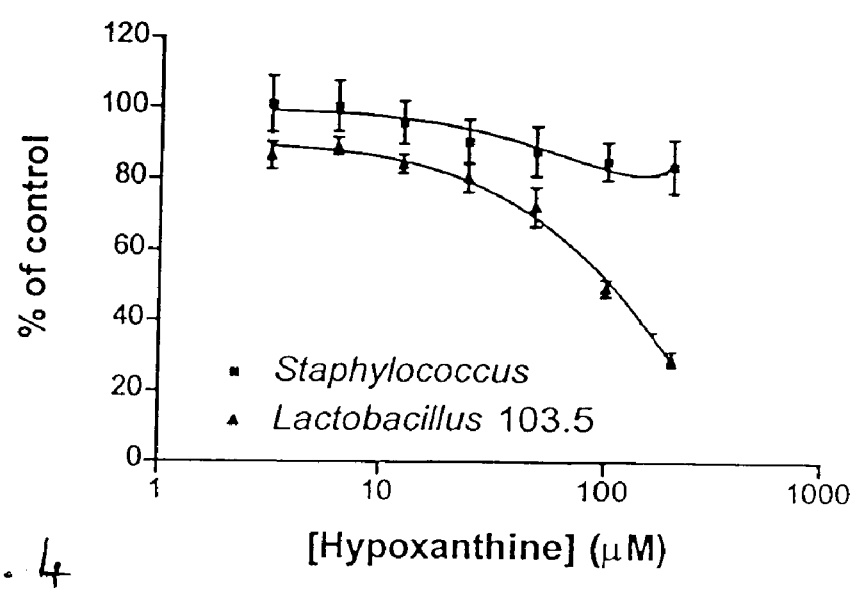
FIG. 4 is a graph showing the dependence of cell growth inhibition on hypoxanthine concentration.

(ii) The growth rate was also measured in relation to the concentration of hypoxanthine, using 30 $\mu$g of XO with cells seeded as described above. FIG. 4 shows the effect of hypoxanthine concentration on bacterial growth. Hypoxanthine in the presence of XO reduced the growth rate of both bacterial species with greatest effect on the Lactobacillus. The half maximal hypoxanthine dose at 30 $\mu$g XO was 103.5 $\mu$M.

Figure 5:
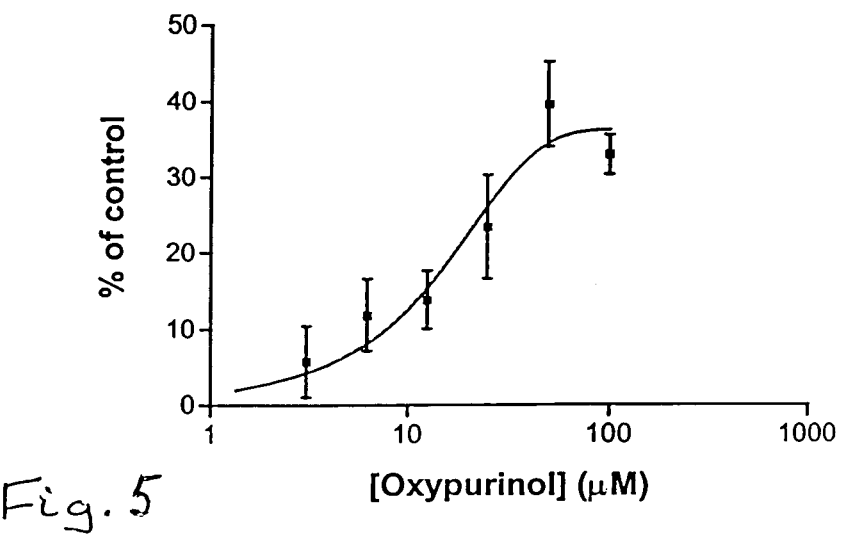
FIG. 5 is a graph showing the effect of oxypurinol on XO/hypoxanthine-related growth inhibition.

(iii) To show that the effect of XO and Hypoxanthine addition was due to the enzymically derived products, oxypurinol at a range of concentrations was added to the cells in the presence of 30 $\mu$g XO and 200 $\mu$M hypoxanthine. FIG. 5 shows its effect on the growth rate of Lactobacillus. Oxypurinol had no effect on growth rate when added at the highest concentration when added alone. However the effect of oxypurinol was to reduce the effect of XO/hypoxanthine growth inhibition in a dose dependent manner.

Figure 6:
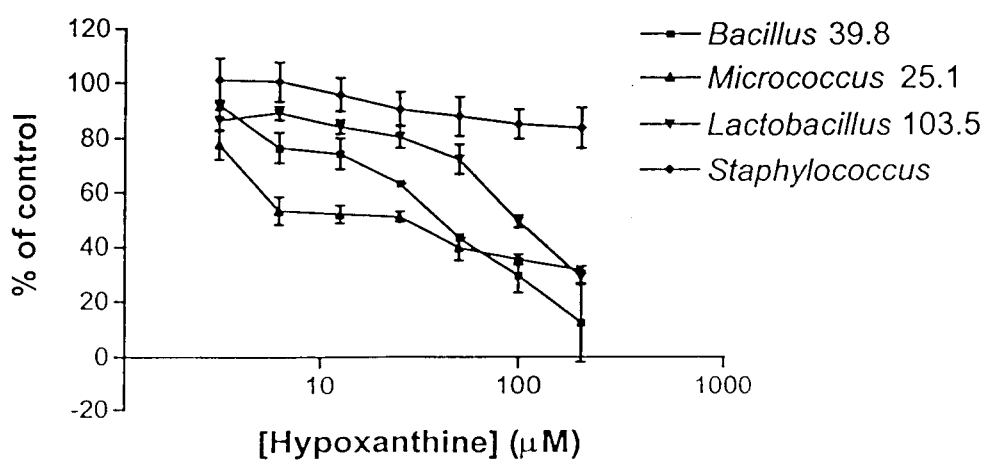
FIG. 6 is a graph showing the effect of hypoxanthine at various concentrations on growth inhibition.

(iv) The effect of XO hypoxanthine addition was measured on the growth rate of a range of bacterial species with 30 $\mu$g XO at varying hypoxanthine concentrations using cells seeded as described above. The results of this study are shown in FIG. 6.

6(e) Effect of $H_2O_2$ and Peroxynitrite on the Growth Rate of Bacteria

To determine the effect of possible enzymically generated radical species cells were grown in the presence of hydrogen peroxide or peroxynitrite. Cells of various species were grown as previously described and a bolus addition of either $H_2O_2$ or peroxynitrite was added at the beginning of logarithmic growth, previous experiments having showed this treatment as the most effective.

The cell growth was determined and plotted against the concentration of $H_2O_2$ or peroxynitrite, as appropriate, and the half maximal concentration of $H_2O_2$ or peroxynitrite was determined. The results are summarised in Table 6, in which corresponding half maximal concentrations for the XO/hypoxanthine system are also given.

TABLE 6

| | Half maximal concentration | | |
|---|---|---|---|
| Species | XO/Hxan ($\mu$M Hypoxanthine) | $H_2O_2$ ($\mu$M) | ONOO - ($\mu$M) |
| Bacillus sp | 39.8 | 77.6 | |
| Micrococcus sp | 25.1 | 19.5 | |
| Lactobacillus casei | 103.5 | 304.8 | 55 |
| Staphylococcus aureus | — | | 290 |

TABLE 6-continued

| | Half maximal concentration | | |
|---|---|---|---|
| Species | XO/Hxan ($\mu$M Hypoxanthine) | $H_2O_2$ ($\mu$M) | ONOO - ($\mu$M) |
| E. coli | | | 1.4 |
| Salmonella enteritidis | | | 2.0 |

As shown in Table 6, the half maximal concentrations for peroxynitrite in respect of Lactobacillus casei is much lower than for $H_2O_2$. In respect of S. aureus, the growth inhibition in the presence of $H_2O_2$ was very limited, with 50% growth reduction not being observed at the concentration ranges used.

Toxicity Test

The toxicity of XOR was investigated by the Standard Patch Test, in which 0.1 ml aliquots of solutions of XO in PBS at concentrations of up to 1 mg/ml were applied to Finn Chamber filter paper. The loaded patches were applied to a portion of skin on the backs of fifteen human subjects predisposed to contact dermatitis. The patches were removed and examined 48 hours after application. The patches were then re-applied and removed and re-examined at 96 hours. No allergic, inflammatory or in any way adverse reaction was observed in any of the subjects tested.

What is claimed is:

1. A pharmaceutical composition comprising
    an amount of XOR effective for treatment or inhibition of lesions, of the human or animal body;
    a pharmaceutically acceptable electron donor system and
    at least one pharmaceutically acceptable excipient or carrier wherein said pharmaceutical composition is a cream, gel or ointment adapted for topical administration to the human or animal body.

2. A composition according to claim 1, adapted for topical administration to the skin.

3. A composition according to claim 1, adapted for topical application to the cornea.

4. A composition according to claim 1, adapted for use in treating or inhibiting ulcers.

5. A composition according to claim 1, for use in the treatment of neoplastically transformed lesions.

6. A composition according to claim 5, for use in treating or inhibiting cervical cancer.

7. A composition according to claim 1, for use in the treatment of virally infected lesions or warts.

8. A composition according to claim 1, for use in the treatment of lesions of the mucous membrane.

9. A composition according to claim 1, in which the xanthine oxidase is in lyophilised form.

10. A composition according to claim 1, wherein said electron donor system comprises at least one nitrogen-containing compound.

11. A composition according to claim 10, wherein said at least one nitrogen-containing compound is a heterocyclic compound.

12. A composition according to claim 11, wherein said nitrogen-containing compound is selected from the group consisting of purines, nicotinamides, and derivatives thereof.

13. A kit for use in the treatment of lesions, having at least two components, a first component of the system comprising a pharmaceutical composition comprising XOR and a second component of the system comprising a pharmaceutical composition comprising a pharmaceutically acceptable electron donor system, said first and second components being arranged for application to a surface of an animal or human body in combination or separately, simultaneously or sequentially, wherein each of the pharmaceutical compositions in the kit is a cream, gel or ointment.

14. A pharmaceutical composition for treating or inhibiting lesions of the human or animal body comprising:

XOR; and at least one pharmaceutically acceptable carrier wherein the composition is a cream, gel, solution ointment adapted for topical administration and comprises from 0.1 $\mu$g to 1 mg XOR per gram of pharmaceutically acceptable carrier.

15. A pharmaceutical composition according to claim 14 further comprising a pharmaceutically acceptable electron donor system.

16. A pharmaceutical composition for topical administration to a human or animal patient, said pharmaceutical composition being a gel or cream comprising XOR.

* * * * *